(12) United States Patent
Schäfer et al.

(10) Patent No.: US 6,579,971 B1
(45) Date of Patent: Jun. 17, 2003

(54) METHOD OF PRODUCING 3,4-DEHYDROPROLINES AND 3,4-DEHYDROPIPERIDINES

(75) Inventors: Bernd Schäfer, Dierbach (DE); Günter Helmchen, Heidelberg (DE); Uli Kazmaier, Wiesloch (DE); Simone Schleich, Heidelberg (DE); Helmut Stahr, Loerrach (DE); Volker Wolfart, Oberentfelden (CH)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/937,312
(22) PCT Filed: Mar. 17, 2000
(86) PCT No.: PCT/EP00/02377
§ 371 (c)(1), (2), (4) Date: Mar. 12, 2002
(87) PCT Pub. No.: WO00/58284
PCT Pub. Date: Oct. 5, 2000

(30) Foreign Application Priority Data
Mar. 26, 1999 (DE) .......................... 199 13 699

(51) Int. Cl.$^7$ ...................... C07K 16/00; C07D 211/32; C07D 211/60; C07D 207/04; C07D 207/46
(52) U.S. Cl. ...................... 530/331; 530/333; 546/225; 546/227; 548/571; 548/572
(58) Field of Search ................ 546/225, 227; 548/571, 572; 530/331, 333

(56) References Cited
U.S. PATENT DOCUMENTS
4,291,040 A * 9/1981 Krapcho .................... 424/263

FOREIGN PATENT DOCUMENTS
WO WO 94/28873 12/1994
WO WO 95/07072 3/1995
WO WO 98/50040 11/1998
WO WO 99/39738 8/1999

OTHER PUBLICATIONS

Meyers et al. "α–Amino Cabanions. Prepartion, Metalation, and Alkylatin of Enamidines. Synthesis of Piperiding and Pyrrolidine Natural Products and Homologation of Carbonyl Compounds" J. Org. Chem. vol. 50 (1985) pp. 1019–1026.
Meyers et al. "α–Amino carganions via Formamidines$^1$ Alkylation of Pyrrolidines, Piperidines, and Related Heterocycles" J. Am. Chem. Soc. Bol. 106, (1984) pp. 3270–3276.
Marchi–Artzner, Valerie et al., "Selective Adhesion Of Endothelial Cells To Artificial Membranes With A Synthetic RGD–Lipopeptide", Chemistry–A European Journal (2001), 7(5), 1095–1101.

* cited by examiner

Primary Examiner—Alan L. Rotman
Assistant Examiner—Raymond Covington
(74) Attorney, Agent, or Firm—Wood, Phillips, Katz, Clark & Mortimer

(57) ABSTRACT

A process for preparing compounds of the formula I

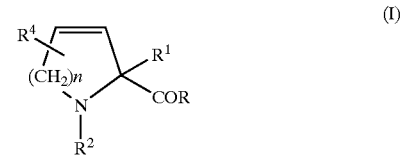

(I)

in which
R is hydrogen, $C_1$–$C_6$-alkoxy, —$NHC_1$–$C_6$-alkyl, —$N(C_1$–$C_6$-alkyl$)_2$, OH, $NH_2$
$R^1$ is hydrogen, $C_1$–$C_6$-alkyl, $Me_3Si$, $C_1$–$C_6$-alkyl-S
$R^2$ is Boc, $C_1$–$C_6$-acyl, mesyl, benzenesulfonyl, tosyl, trifluoroacetyl, A1–A3-peptide
n is 1, 2
$R^4$ is H, $C_1$–$C_6$-alkyl,
is described.

6 Claims, No Drawings

METHOD OF PRODUCING 3,4-DEHYDROPROLINES AND 3,4-DEHYDROPIPERIDINES

This application is a 371 of PCT/EP00/02377 filed Mar. 17, 2000.

The present invention relates to a process for preparing 3,4-dehydroprolines and 3,4-dehydropiperidines. In particular, the invention relates to a process for preparing compounds of the formula I

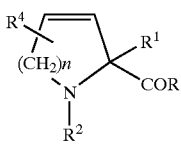

in which
R is hydrogen, $C_1$–$C_6$-alkoxy, —$NHC_1$–$C_6$-alkyl, $N(C_1$–$C_6$-alkyl$)_2$, OH, $NH_2$
$R^1$ is hydrogen, $C_1$–$C_6$-alkyl, $Me_3Si$, $C_1$–$C_6$-alkyl-S
$R^2$ is Boc, $C_1$–$C_6$-acyl, mesyl, benzenesulfonyl, tosyl, trifluoroacetyl, A1–A3-peptide
n is 1, 2
$R^4$ is H, $C_1$–$C_6$-alkyl.

3,4-Dehydroprolines are prepared starting from 4-hydroxyproline via the Tschugaeff reaction (P. Grogg, Angew. Chem. 92 (1980) 761). In addition to relatively poor yields (64%), this method requires highly toxic compounds to be handled, such as carbon disulfide, methyl iodide and methyl mercaptan. The pyrolytic decomposition at from 180 to 190° C. and 12 Torr requires more complex technology.

Instead of the xanthogenates, it is also possible to react corresponding iodides, sulfoxides or selenium oxides by thermolysis (J.-R. Dormoy, Synthesis (1982) 752). However, this does not solve the fundamental problems regarding toxicity and technical expense.

Achiral syntheses usually use pyrrolecarboxylic acid as starting material, which is reduced using phosphonium iodide/hydrogen iodide (J. W. Scott, Synth. Commun. 10 (1980) 529). The racemate is then separated by crystallization using chiral amines (S. S. Kerwar, J. Bio. Chem. 251 (1976) 503; U.S. Pat. No. 4,066,658) or tartaric acid (A. Corbella, Chem. Ind. (1969) 583). This synthesis has the disadvantages that highly toxic phosphane has to be handled, and that the maximum yield for the resolution of the racemate is 50%.

WO 98/04523 describes the elimination of sulfonic esters of hydroxyproline ester and subsequent enzymatic resolution of the racemate.

Until recently, the Birch reduction of pyrrole derivatives was not known. In J. Org. Chem. 61 (1996) 7664 T. J. Donohoe describes, for the first time, the achiral Birch reduction of pyrrole-2-carboxylic acid derivatives. As described above, up to now it was only possible to separate them into the enantiomers by classical or enzymatic resolution of the racemate.

WO 98/55456 describes the diastereoselective Birch reduction of chiral pyrrole-2-carboxylic esters and pyrrole-2-carboxamides.

The synthesis of 3,4-dehydropiperidine-2-carboxylic acid derivatives is described in D'Ambra, Bell, J. Org. Chem. 54 (1989) 5632, and in Krogsgaard-Larsen, J. Labeled Compd. 19 (1982) 689. Both syntheses require extremely toxic chemicals (isocyanates, nitrosamines) to be handled and afford the desired product only in poor yields.

It is an object of the present invention to prepare 3,4-dehydroprolines and 3,4-dehydropiperidines of the formula I using a simple reaction sequence.

The preparation of 3-pyrroline, for example via metathesis, is comprehensively documented in the more recent literature (Grubbs, J. Org. Chem. 62 (1997) 7310; Pandit, Tetrahedron Lett. 37 (1996) 547; Grubbs, J. Am. Chem. Soc. 115 (1993) 9856; Moreno-Manas, Tetrahedron 54 (1998) 14869).

Alkylations of 3-pyrroline in the 2 position, for example Meyers, J. Am. Chem. Soc. 107 (1985) 7974; Macdonald, J. Org. Chem. 45 (1980) 193; Francke, Liebigs Ann. (1995) 193, and the hydroformylation which affords derivatives of proline (Izawa, Bull. Chem. Soc. Jpn. 64 (1991) 620) are known.

Carboxylations of pyrrolidine are known very well, for example Beak, J. Am. Chem. Soc. 116 (1994) 3231. However, Colegate, Austral. J. Chem. 37 (1984) 1503 teaches that, in an analogous deprotonation of methoxycarbonyl-3-pyrroline, this compound undergoes an undesirable intermolecular reaction, giving N-methoxycarbonyl-3-pyrroline-2-carboxylic acid 1-(3-pyrrolinide) in a yield of 65%.

Surprisingly, it has been found that pyrrolines and 3,4-dehydropiperidines of the formula II

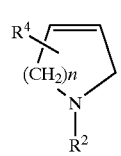

in which
$R^2$ is Boc, $C_1$–$C_6$-acyl, mesyl, benzenesulfonyl, tosyl, trifluoroacetyl, A1–A3-peptide
$R^4$ is H, $C_1$–$C_6$-alkyl
n is 1 or 2
can be reacted in the presence of a carboxylating agent or carbonylating agent of the formula III

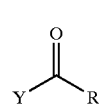

in which
R is hydrogen, $C_1$–$C_6$-alkoxy, —$NHC_1$–$C_6$-alkyl, —$N(C_1$–$C_6$-alkyl$)_2$, OH, $NH_2$
Y is Cl, $C_1$–$C_6$-alkoxy, —$NHC_1$–$C_6$-alkyl, —$N(C_1$–$C_6$-alkyl$)_2$, $N(C_1$–$C_6$-alkyl)$OC_1$–$C_6$, where R is not OH,
or, for R=OH in formula I, with $CO_2$, together with a strong base, preferably an alkali metal amide, and, if appropriate, hydrolyzed or reacted with an agent of the formula IV

 $R^3$—X (IV)

in which
X is Cl, Br, I, MesO, TosO, triflate
$R^3$ is hydrogen, $C_1$–$C_6$-alkyl, $Me_3Si$, $C_1$–$C_6$-alkyl-S or $NH_4$ or
$R^3$—X is $(C_1$–$C_6$-alkyl-S$)_2$
to give the desired dehydroprolines and dehydropiperidines in good yields.

Preferred alkali metal amides are lithium amides and sodium amides of the formula V $$MNR^5R^6 \quad (V)$$

where
M is Na, Li,
$R^5$ is H, $C_1$–$C_6$-alkyl
$R^6$ is H, $C_1$–$C_6$-alkyl.

The preferred meaning of the formula III is di-$C_1$–$C_6$-alkyl carbonate, in particular dimethyl carbonate and diethyl carbonate.

A1–A3-peptide is to be understood as meaning a radical comprising up to three amino acids, the amino acids being natural (proteinogenic) and unnatural (nonproteinogenic) amino acids. The A1–A3 peptide can be derivatized or protected by customary protective groups. A1–A3-peptide includes partially or fully peptidomimetic structures.

A1, A2 and A3 are to be understood as meaning, in particular, the following amino acids: t-butylglycine, t-butylalanine, adamantylglycine, adamantylalanine, natural amino acids, their D-enantiomers, cyclopropylglycine, cycloheptylglycine, cycloheptylalanine, cyclobutylglycine, cyclopentylglycine, cyclohexylglycine, cyclopropylalanine, cyclobutylalanine, cyclopentylalanine, cyclohexylalanine, all isomers of furanylglycine, furanylalanine, naphthylglycine, naphthylalanine, thiophenylglycine, thiophenylalanine, isoquinolineglycine, isoquinolinealanine, quinolineglycine, quinolinealanine, pyrrolylglycine, pyrrolylalanine, imidazolylglycine, imidazolylalanine, 3,4-dehydroproline.

The reaction is carried out in solvents which are inert under the reaction conditions. Preferred solvents are $C_2$–$C_8$ hydrocarbons, in particular hexanes, THF and $C_1$–$C_6$-ethers, $C_1$–$C_6$-ether/DMPU mixtures, dioxane and mixtures of the solvents mentioned.

The reaction is generally carried out at from −100 to +100° C. and in a pressure range from 1 to 200 bar. Preference is given to a temperature range of from −20 to +20° C.

In general, the reaction is terminated in a customary manner when it is no longer possible to detect pyrroline derivatives or dehydropiperidine derivatives in the reaction mixture (for example by GC, HPLC, TLC).

Work-up to give the product of the process is generally carried out by customary methods, such as distillation, filtration, centrifugation or extraction.

The process according to the invention is carried out batchwise, for example in a stirred reactor. However, the fact that the process can be carried out in a simple manner offers the advantage of making it possible to convert it to continuous operation, for example using a reaction tube or a stirred-reactor cascade.

If desired, the resulting crude products can be purified further, for example by crystallization, extraction or chromatography.

The 3,4-dehydroprolines and 3,4-dehydropiperidines of the formula I which can be prepared in a simple manner by the process according to the invention are useful intermediates for the synthesis of dyes, crop protection agents or drugs, in particular thrombin inhibitors, as described above, for example, in the publications WO 94/29336, WO 95/35309, WO 96/17860, WO 96/24609, WO 96/25426, WO 98/06741.

EXAMPLES

Example 1

Methyl N-$^t$butoxycarbonyl-$\Delta^3$-dehydroprolinate 4.1 ml (48.7 mmol) of dimethyl carbonate and 8.2 g (48.5 mmol) of N-$^t$butoxycarbonyl-$\Delta^3$-pyrroline were dissolved in 40 ml of THF, and the mixture was cooled to approximately −5° C. 54 ml of a solution of LDA (2 molar in heptane, THF, ethylbenzene) were then added dropwise such that the internal temperature did not exceed 4° C. After about 20 minutes, the addition was complete. The color of the reaction mixture had changed to red-brown. The reaction mixture was stirred at 0° C. for another 10 minutes and then diluted with 150 ml of n-pentane, and the mixture was poured into 200 ml of 1 N HCl. The phases were separated, the aqueous phase was extracted 3 times with 50 ml of n-pentane each time and the combined organic phases were washed successively in each case twice with 0.01 N HCl, saturated NaHCO$_3$ solution and saturated NaCl solution. The organic phases were then dried over MgSO$_4$, and the volatile components were removed using a rotary evaporator.

The yellow-brown crude product was distilled at 120° C.–150° C./0.4 Torr. This gave a slightly yellow oil which crystallized when seed crystals were added. For the final purification, the crystals were recrystallized from n-pentane. Yield: 9.06 g; 82% of theory; colorless clear crystals.

Example 2

Methyl N-$^t$butoxycarbonyl-2-methyl-$\Delta^3$-dehydroprolinate

Methyl N-$^t$butoxycarbonyl-$\Delta^3$-dehydroprolinate was prepared as described in Example 1 (batch size 1.60 mmol=271 mg of N-$^t$butoxycarbonyl-$\Delta^3$-pyrroline. After all the lithium diisopropylamide had been added, the mixture was stirred at 0° C. for 5 minutes. At this temperature, 0.1 ml (1.61 mmol) of methyl iodide was then added. The mixture was then stirred at 0° C. for 10 minutes and subsequently worked up as under Example 1. This gave 320 mg (83% of theory) of a brown oil which, according to analysis by gas chromatography, contained 24% of methyl N-$^t$butoxycarbonyl-$\Delta^3$-dehydroprolinate and 75% of the desired product.

Example 3

Methyl N-ethoxycarbonyl-$\Delta^3$- piperidine-2-carboxylate

A solution of 228 mg (1.47 mmol) of N-ethoxycarbonyl-$\Delta^3$-piperidine and 0.14 ml (1.66 mmol) of dimethyl carbonate in 3 ml of THF was cooled to 0° C. and subsequently admixed dropwise with 1.5 ml of LDA solution (2 molar in heptane, THF, ethylbenzene). This reaction mixture was stirred at 0° C. for 10 minutes and subsequently poured into a mixture of 5 ml of 1 N HCl and 10 ml of tert-butyl methyl ether. The phases were separated, the aqueous phase was extracted 3 times with 10 ml of n-pentane each time and the combined organic phases were washed successively in each case twice with 0.01 N HCl, saturated NaHCO$_3$ solution and saturated NaCl solution. The organic phases were then dried over MgSO$_4$ and the volatile components were removed using a rotary evaporator. The crude product was subsequently chromatographed over silica gel (mobile phase petroleum ether:ethyl acetate 8:2). Yield: 201 mg of a colorless oil (64% of theory).

Example 4

Methyl N-t-butoxycarbonyl-(R)-cyclohexylglycinyl-(R,S)-dehydroprolinate

An LDA solution (2M, 2.6 mmol—Fluka) was added dropwise to a solution, cooled to 0° C., of N-t- butoxycarbonyl-(R)-cyclohexylglycinylpyrroline (524 mg, 1.70 mmol) and dimethyl carbonate (0.3 ml, 357 mmol) in 5 ml of dry THF. The reaction mixture was stirred at 0° C. for 15 minutes and then poured into 1N HCl/n-pentane, washed with NaHCO$_3$ solution and brine and then dried over MgSO$_4$. The solvent was removed using a rotary evaporator, giving 0.59 g of a yellow oil. Final purification was carried out by silica gel chromatography using PE:EA 7:3 as mobile phase. White, tacky solid. Yield: 307 mg (49% of theory).

What is claimed is:

1. A process for preparing 3,4-dehydroprolines and 3,4-dehydropiperidines of the formula I

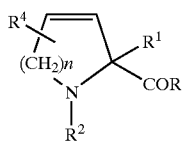

(I)

in which

R is hydrogen, C$_1$–C$_6$-alkoxy, —NHC$_1$–C$_6$-alkyl, —N(C$_1$–C$_6$-alkyl)$_2$, OH, NH$_2$ R$^1$ is hydrogen, C$_1$–C$_6$-alkyl, Me$_3$Si, C$_1$–C$_6$-alkyl-S R$^2$ is Boc, C$_1$–C$_6$-acyl, mesyl, benzenesulfonyl, tosyl, trifluoroacetyl, A1–A3-peptide n is 1, 2

R$^4$ is H, C$_1$–C$_6$-alkyl comprising the steps of reacting a pyrroline or dehydropiperidine derivative of the formula II

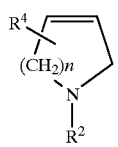

(II)

with a strong base and a compound of the formula III

(III)

in which

Y is Cl, C$_1$–C$_6$-alkoxy, —NHC$_1$–C$_6$-alkyl, —N(C$_1$–C$_6$-alkyl)$_2$, N(C$_1$–C$_6$-alkyl)OC$_1$–C$_6$, where R is not OH, or with carbon dioxide for R=OH and hydrolyzing the reaction product of II and III or with a compound of the formula IV

R$^3$—X  (IV)

in which

X is Cl, Br, I, MesO, TosO, triflate

R$^3$ is hydrogen, C$_1$–C$_6$-alkyl, Me$_3$Si, C$_1$–C$_6$-alkyl-S or NH$_4$ or R$^3$—X is (C$_1$–C$_6$-alkyl-S)$_2$.

2. A process as claimed in claim 1 where the strong base is an alkali metal amide.

3. A process as claimed in claim 1 where the compound III is di-C$_1$–C$_6$-alkyl carbonate.

4. A process as claimed in claim 1 wherein A1–A3-peptide represents all enantiomeric or diastereomeric forms.

5. A process as claimed in claim 1 wherein, in the case of chiral radicals R$^2$, one diastereomer may be formed in excess.

6. A process as claimed in claim 1 wherein the reaction is carried out in a pressure range of from 1 to 200 bar at a reaction temperature between −100 and +100° C.

* * * * *